United States Patent
Buttner et al.

(10) Patent No.: US 8,105,539 B2
(45) Date of Patent: Jan. 31, 2012

(54) CHEMICAL SENSOR FOR HYDRAZINE

(75) Inventors: William J. Buttner, Merritt Island, FL (US); Joseph R. Stetter, Hayward, CA (US)

(73) Assignee: KWJ Engineering, Newark, CA (US)

( * ) Notice: Subject to any disclaimer, the term of this patent is extended or adjusted under 35 U.S.C. 154(b) by 610 days.

(21) Appl. No.: 11/842,281

(22) Filed: Aug. 21, 2007

(65) Prior Publication Data
US 2009/0053104 A1 Feb. 26, 2009

(51) Int. Cl.
*G01N 21/01* (2006.01)
(52) U.S. Cl. ............... 422/82.06; 422/82.05; 422/82.09; 204/412; 204/415; 204/411; 204/406
(58) Field of Classification Search ............... 204/1, 195, 204/411, 412, 406, 415; 324/29; 422/82.06, 422/82.05, 82.09
See application file for complete search history.

(56) References Cited

U.S. PATENT DOCUMENTS 4,123,700 A * 10/1978 LaConti et al. ............... 324/425
4,326,927 A * 4/1982 Stetter et al. ............... 205/780.5

OTHER PUBLICATIONS

Dee et al. Lyndon B. Johnson Space Center, Houston, TX Dec. 1, 2004 online publication.*
wordnetweb.princeton.edu/perl/webwn definition of "reagent".*

* cited by examiner

*Primary Examiner* — Sally Sakelaris
(74) *Attorney, Agent, or Firm* — Dinsmore & Shohl LLP

(57) ABSTRACT

Chemical sensors whose active element exhibits both a visual change in color and a measurable change in electrical resistance when exposed to an analyte to which it selectively reacts are provided. These sensor have several unique features including vastly improved stability measured in years, irreversible visual changes and surprisingly reversible electrical changes. The combined unique features enable a new generation of ultra low power alerting, alarming and readout devices for hydrazines and other strongly reducing chemicals.

23 Claims, 6 Drawing Sheets

HYDRAZINE CHEMICAL SENSOR

Left Side: Exposed to HZ. A dark color forms and the device is very conductive

Right Side: Unexposed. The device is a light yellow color and is very resistive.

FIGURE 1 - (Prior Art)

HYDRAZINE CHEMICAL SENSOR

Left Side: Exposed to HZ. A dark color forms and the device is very conductive

Right Side: Unexposed. The device is a light yellow color and is very resistive.

FIGURE 3

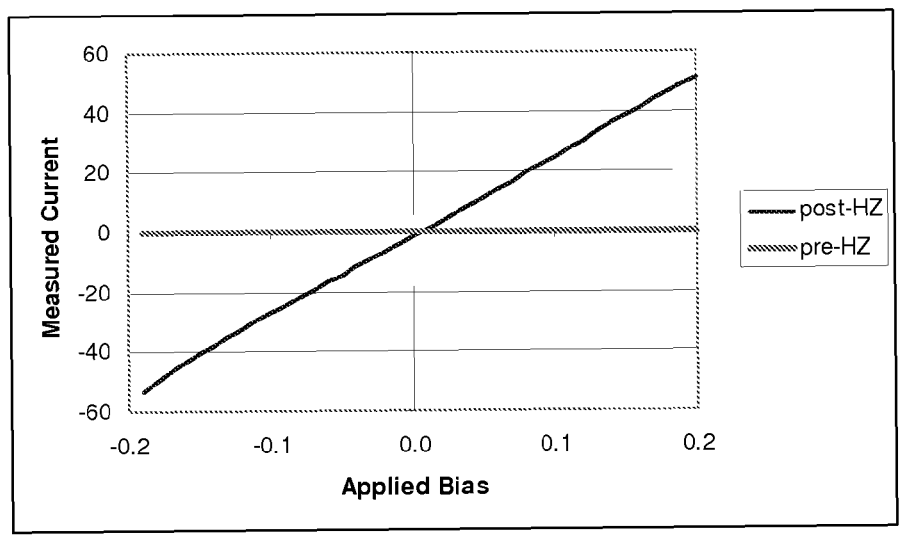

CONDITIONS:
1. Bias varied from −200 mV to +200 mV in 10 mV steps. The current is plotted as microamps
2. The sensors were tested before (pink) and after exposure (dark blue) to HZ vapors
3. Vapor exposure was for about 1 hour in a sealed jar
4. The Gamry measured a resistance of 400 ohms (Pins 1 and 2) for the post exposure sensor
5. Prior to vapor exposure, the Gamry could not obtain a measurable resistance.

CHEMICAL SENSOR FOR HYDRAZINE

TECHNICAL FIELD

The present invention is directed to chemical sensor devices that exhibit their response to the chemical with multiple recordable changes in the chemically sensitive layer. In this case, the chemical hydrazine causes a response in the sensor layer that results both a visual or optical change, e.g., the color changes, and a readily measured change in electrical resistance of the film when exposed to an analyte. Toxic gas sensors with multiple measurands, especially if the responses are orthogonal or only partially correlated, possess more analytical information capability and have often surprising useful features.

BACKGROUND

Hydrazine is a highly toxic, yet common component of hypergolic rocket fuel that is used by both NASA Shuttle and DOD missile systems and used routinely in industrial processes. Hydrazine, monomethylhydrazine, and unsymmetric hydrazine are routinely used and often collectively referred to as the hydrazines (HZ). As a routinely-used toxic chemical, permissible exposure levels (PEL) are highly regulated. Although the Occupational Safety and Health Administration (OSHA) PEL level for hydrazine is 1 ppm, American Conference of Industrial Hygienists (ACGIH) has recommended that the level be lowered to 10 ppb. The administrative levels at the Kennedy Space Center follow the more stringent maximum exposure limit of 10 ppb recommended by ACGIH. Thus, personal exposure and workplace monitoring is required to assure worker safety and workplace compliance to government standards.

There are numerous existing technologies for measuring HZ, including electrochemical, metal oxide, photo-ionization detector (PID), mass spectrometer (MS), and Infrared (IR) sensors. In general, electronic monitors adapted to measure hydrazine vapors often tend to be expensive, require considerable manual maintenance, are plagued with responses from numerous interferants and/or lack of stability or sensitivity or selectivity (e.g., see "Electronic Nose for Space Program Applications" Rebecca C. Young, William J. Buttner, Bruce E. Linnell, and Rajeshuni Ramesham, *Sensors and Actuators* 93 (2003) 7-16). Passive colorimetric devices also exist for detecting hydrazine vapors. However, these devices either require a bulky and power hungry optical reader for triggering an alarm or require that operators get within eyesight of the indicator (typically less than 2 meters), which means operators can be exposed to the vapor while reading the indicator or must be dressed in cumbersome expensive protective equipment to read the monitor.

Accordingly, there is a need for improved chemical sensors devices.

SUMMARY OF THE INVENTION

Embodiments of the present invention are directed to chemical resistor sensors comprising: (1) a film layer comprising at least one chemical reagent dispersed in a medium and (2) a substrate layer comprising at least two electrodes, wherein the chemical reagent upon interaction with an analyte reacts to produce both a visual change and an electrical response. Either visual change or electrical change can be used to measure the presence and amount of the target analyte. The chemical reagent can be controlled to optimize reactivity toward the analyte and the range of responses.

Embodiments of the present invention are also directed to chemical resistor sensors comprising: (1) a film layer comprising at least one noble metal salt dispersed in a polymer medium and (2) a substrate layer comprising at least two electrodes, wherein the noble metal salt upon interaction with an analyte reacts to produce a visual change and an electrical response. Either visual/optical or electrical means can be used to detect the sensor response and provide readout of the presence or amount of the analyte.

Embodiments of the present invention are further directed to chemical resistor sensors comprising: (1) a film layer comprising potassium tetrachloroaurate ($KAuCl_4$) dispersed in a polymer medium and (2) a substrate layer comprising at least two electrodes, wherein the potassium tetrachloroaurate upon interaction with hydrazine vapor or a derivative thereof reacts to produce a visual change and an electrical response.

BRIEF DESCRIPTION OF THE FIGURES

The following Detailed Description may be more fully understood in view of the figures, in which:

FIG. 3 is a graph depicting I-V characteristic of a chemical resistor sensor prior to and following exposure to hydrazine vapors;

Figure 1:
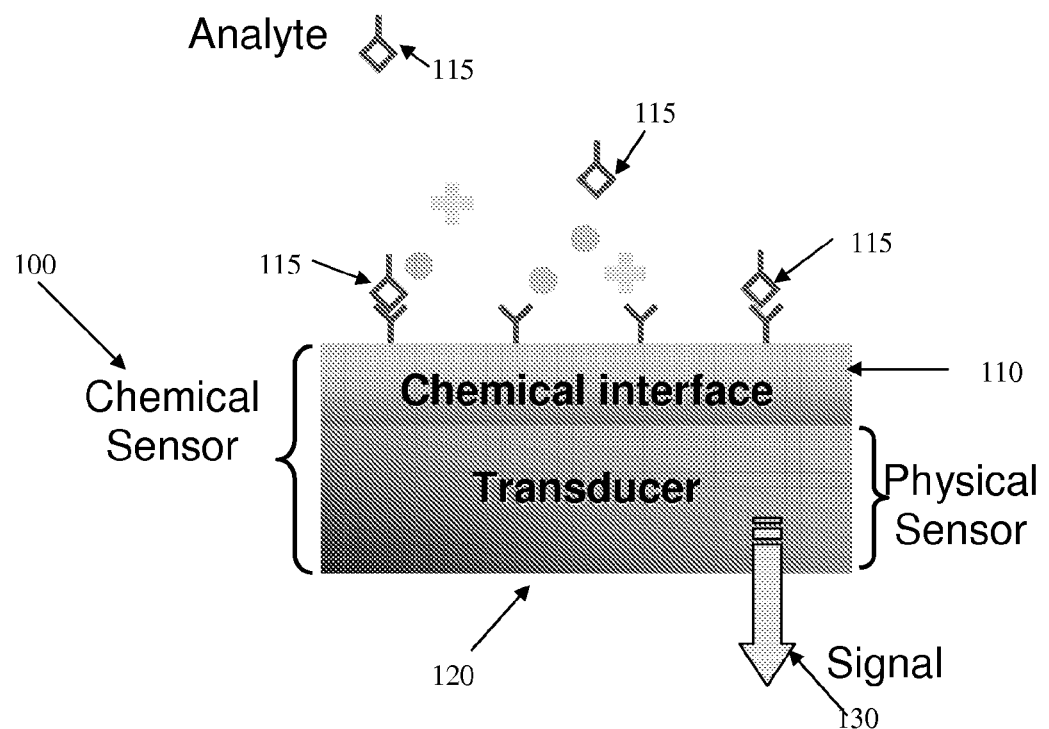
FIG. 1 is a schematic representation of a prior art chemical sensor.

The embodiments set forth in the drawings are illustrative in nature and are not intended to be limiting of the invention defined by the claims. Moreover, individual aspects of the drawings and the invention will be more fully apparent and understood in view of the detailed description.

DETAILED DESCRIPTION OF THE ILLUSTRATIVE EMBODIMENTS

The present invention is directed to chemical resistor sensor devices whose active element selectively reacts with an analyte to produce both a visual change in color of the active element and a change in electrical resistance of the chemical sensor device. The device herein is based upon the electrochemical reducing powers of the analyte, such as hydrazine or a derivative thereof, to transform a chemical reagent, such as dry gold salt (potassium tetrachloroaurate, KAuCl4) and analogous noble metal salts, into sub-micron sized metallic particles. The transformation in the chemically reactive element of the device can then be measured by the change in electrical resistance or the change in optical properties. In theory, the weight of the element, the magnetic properties, and other thermal properties might also change but may require different readout transducers than exemplified here.

A chemical sensor can be defined as a small self-contained integrated system of parts that, as the result of a chemical interaction or process between the analyte and the device, transforms chemical or biochemical information of a quantitative or qualitative type into an analytically useful signal.

As such, we can define in general as depicted in FIG. 1, a chemical sensor 100 as a device comprising of a chemically sensitive layer, or chemical interface (CI) layer 110, that interacts with the target analyte 115 that is interfaced with the transducer readout layer 120. Sometimes the chemically sensitive layer 110 and the transducer readout layer 120 are combined, for example, a heated metal oxide layer which interacts with the gas, and subsequently changes resistance. Sometimes the chemically sensitive layer 115 is distinct from the transducer readout layer 120 as is the case with mechanical sensor platforms like the QCM [quartz crystal microbalance] device in which a target analyte reacts/absorbs in the chemically sensitive layer which is located on the QCM surface and then the resonant frequency of the QCM changes. In both examples, a pair of electrodes located appropriately in or on the sensor readout the signal 130. In a optical evanescent wave fiber optic sensor, the chemically sensitive layer is placed on the surface of the fiber. When light is passed through the fiber, it is differently attenuated, depending upon the analyte interaction with the CI layer. The major point here is that a chemical sensor has a chemical interface layer that controls the reactivity with the analyte and a transducer or means to readout the changes in the CI layer that can be electrical, optical, mechanical, electrochemical, magnetic, or mechanical.

One recently developed colorimetric indicator for hydrazine is based upon the chemical reduction between hydrazine and a dry gold salt (potassium tetrachloroaurate, KAuCl4). See "Indicator Devices for Detection of Trace Gaseous Hydrazines" L. Dee, B. Greene, D. Baker, JANNAF 18$^{th}$ Safety & Environmental Protection Subcommittee Meeting, CPIA Publication 698 May 2000. The actual transduction process for the irreversible color change is via a spontaneous redox chemical reaction with hydrazine, which transforms the yellow gold III salt into black, submicron particles of reduced gold. The color change after exposure with hydrazine or a derivative thereof is irreversible. In this colorimetric indicator, the pure salt was simply applied to an inert substrate, typically glass-fiber filter paper; which is done by immersing the filter paper into an aqueous solution of the salt, removing and allowed to dry. Upon drying, the filter paper can be configured into indicator patches for deployment and the Au is dispersed on the filter paper medium. See "Color-Indicating Patch for Shuttle Auxiliary Power Unit Hydrazine Transfer Line" William J. Buttner and Rebecca C. Young, NASA Kennedy Space Center Research and Technology 2003 Annual Report, NASA-TM-2003-211190, pg 6-7 and "Wipes, Coatings, and Patches for Detecting Hydrazine, NASA Tech Briefs, 29 #12 pp. 49-51 (2005). The transformation of the salt from insulator to electronic conductor was not yet recognized for either work of these prior work. But surprisingly, when the salt film was placed on a substrate with two electrodes, a significant change in conduction was observed even when the particles were dispersed in a matrix.

The chemical sensors of the present invention are passive chemical sensors with a readout of impedance change upon exposure to the target hydrazine analytes, which may be configured to draw electric power only after the chemical reagent is exposed to the analyte. For example, a device in Au-salt form has very high impedance at the start and therefore only tiny currents are observed when the device is placed on power [a few volts]. In this "ready to react" mode, the device draws very tiny current and uses nearly zero power and can remain ready to react, alert, and/or alarm for a very long time even on a small battery or power scavenger circuits.

Figure 5:
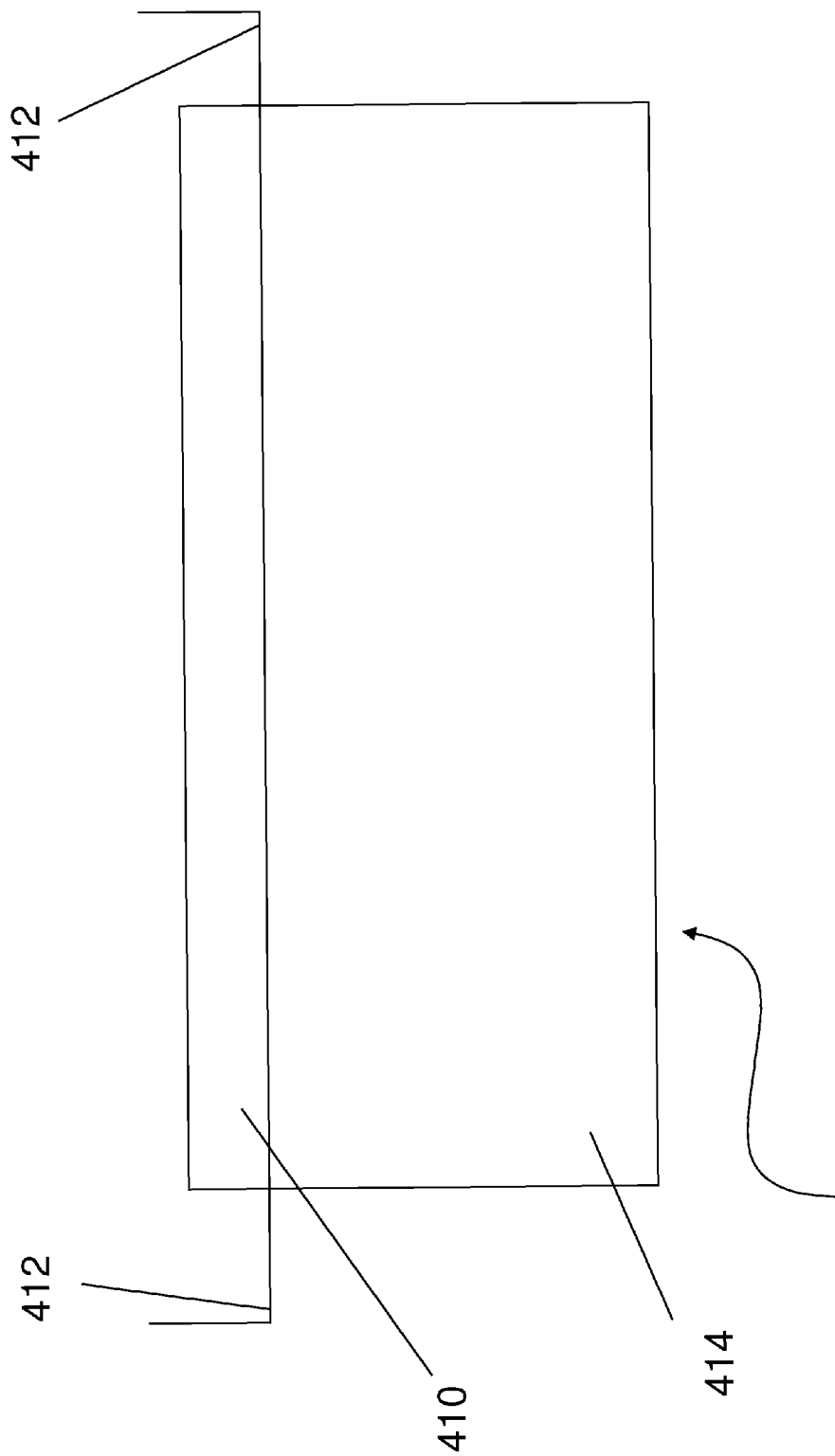
FIG. 5 is a chemical resistor sensor according to one embodiment of the present invention.

Referring to FIG. 5, in one embodiment of the present invention, the chemical resistor sensor 405 comprises: (1) a film layer 410 comprising at least one chemical reagent dispersed in a medium and (2) a substrate layer 414 comprising at least two electrodes 412, wherein the chemical reagent upon interaction with an analyte reacts to produce a visual change and an electrical response. The chemical resistor sensor 405 may be characterized as an electrical insulator prior to exposure of the analyte. Following exposure of the analyte with the chemical reagent, the chemical resistor sensor 405 transforms into a conductor. One skilled in the art of making alarms will appreciate the utility of a low power sensor that can operate for years in a ready mode on a tiny battery or environmental power scavenger.

One skilled in the art will appreciate the various chemical reagents that may be employed in the chemical resistor sensors of the present invention. Examples include, but are not limited to noble metal salt and derivatives thereof. In one embodiment, the noble metal salt comprises potassium tetrachloroaurate ($KAuCl_4$) or a derivative thereof. The chemical reagent employed in the chemical resistor sensor selectively reacts with an analyte. Accordingly, the chemical reagent employed in the chemical resistor sensor will be selected depending upon the analyte that the chemical sensor resistor will be detecting. As such, one skilled in the art will appreciate which chemical reagent should be employed in the chemical resistor sensor in order to selectively react with a particular analyte. For example, in one embodiment, if the chemical reagent comprises potassium tetrachloroaurate ($KAuCl_4$) or a derivative thereof, then the analyte may comprise hydrazine vapor or a derivative thereof as the analyte. Derivatives of hydrazine include, but are not limited to, hydrazine, monomethyl hydrazine and unsymmetrical dimethyl hydrazine.

To one skilled in the art, there may be other gold salts or compounds or mixtures of compounds that will cause a reaction with hydrazines to form a differently conductive layer, and hence make possible an electrical readout and/or cause a reaction to obtain a color change and make possible an optical readout by human sight or an optical transducer. Similarly, we expect that our reactive salt is reduced by the hydrazines and may also be reduced by other reducing compounds like tetraflouroborates or even hydrogen if the temperature was a bit elevated. So it is possible to envision other target analytes for this approach and other possible chemically sensitive layers that result in the multiple [2 or more] simultaneously measurable parameters.

At least one chemical reagent is dispersed in a medium to form the film layer of the chemical resistor sensor. The medium provides an inert physical matrix to contain the chemical reagent while still allowing the analyte access to the chemical reagent. As such, in certain embodiments, the film layer may be permeable. While not wishing to be bound by theory, it is believed that the medium improves the mechanical stability, chemical stability, responsiveness, reliability, design options, and manufacturability of the sensor. The medium can also provide improved resistance to fluctuating environmental parameters (e.g., irradiance levels, temperature fluctuations and humidity). Moreover, improved kinetics and sensitivity can be achieved by selecting a medium that is compatible with the analyte to be detected. The chemical sensor can be adjusted for range of operation, concentrations, and performance. The surprising result is the stabilizing and/or sensitivity afforded by the medium, which can be further optimized and might include a variety of phase materials from polymer to crystalline and organic to inorganic materials. One skilled in the art will appreciate the various mediums that may be used, any of which may be employed herein. In one embodiment, the medium comprises a stabilizing and/or a dielectric medium. In other embodiments, the medium comprises a polymer medium. Suitable polymers include, but are not limited to, polystyrene, polyethylene or a combination thereof. However, it is noted that in certain embodiments, the medium may not be required for certain applications. While not being limited to a theory, it is believed that the stability of the chemically sensitive layer used herein is a very important and surprising advance of this technology that is caused by the addition of the polymer [stabilizing means] in the matrix. And not only does it provide stability, how this happens we are not certain, but it provides some measure of reversibility of the reaction. For example, the exposed sensor is reversed by exposure to an oxidant [oxygen in the air], but the color does not reverse whereas the electrical resistance becomes high again. And upon exposure to hydrazines, the resistance becomes low once again. Thus the electrical effect is reversible and the optical effect is not. Applicants have invented a sensor device which is surprisingly both reversible and stable whereas all known prior devices are irreversible.

As defined herein, "dispersed" includes any process in which at least one chemical reagent is combined with a medium to form a film layer for the chemical resistor sensor. Processes for dispersing the at least one chemical reagent in the medium include, but are not limited to, mixing, embedding and/or dissolving. In one embodiment, the film layer may be formed by the process comprising: (1) dissolving a medium in a solvent to form a dissolved medium; (2) adding the chemical reagent to the dissolved medium to form a mixture; (3) applying the mixture to the substrate layer; and (4) evaporating the solvent in the mixture to form the film layer on the substrate layer. One skilled in the art will also appreciate the various solvents that may be used to form the dissolved medium discussed in detail above. In one embodiment, the solvent is dimethylformamide (DMF).

One skilled in the art will further appreciate the various concentrations of the chemical reagent in the film layer, which may be employed to detect a particular analyte. In one embodiment, the chemical reagent comprises from about 2 to about 10 weight percent of the medium. In other embodiment, the ratio of the chemical reagent to the medium is about 1 to about 1.

As noted above, the chemical resistor sensor comprises a substrate layer. One skilled in the art will appreciate the various materials that may be used as the substrate layer, any of which may be employed herein. In one embodiment, the substrate layer comprises at least two electrodes. In another embodiment, the substrate layer comprises interdigitated electrodes of Pt alumina. The interdigitated electrode substrate layer may comprise various sizes. In one embodiment, the interdigitated electrode substrate layer is about 10 microns wide and about 1000 microns long. In another exemplary embodiment, the substrate could also contain an optical fiber to enable an optical readout of the visual change in the film.

The actual transduction process for color change of the chemical reagent and resistance change of the chemical sensor is via a spontaneous electroreduction reaction with the analyte. As noted above, prior to exposure, the chemical resistor sensor is essentially an insulator [when a non-conducting polymer is used and the Au-salt is not electronically conducting], while post-exposure [the conducting Au metal particles are formed by reaction of the salt with the target hydrazines reducing agent] resistance is decreased by over a factor of 1000. The actual resistance change is predicated upon geometry and salt/polymer ratio and other optimization parameters. In certain embodiments, the electrical resistance prior to the reaction is greater than about 10 MΩ and the electrical resistance after the reaction is from about 50 to less than about 5000Ω. In other embodiments, the electrical resistance prior to the reaction is greater than about 1 MΩ and the electrical resistance after the reaction is less than about 50Ω. The reaction may initiate within seconds and may be completed in about 5 minutes. However, the time in which the reaction will occur and will be complete will be dependent upon the components that comprise the chemical resistor sensor.

Figure 6:
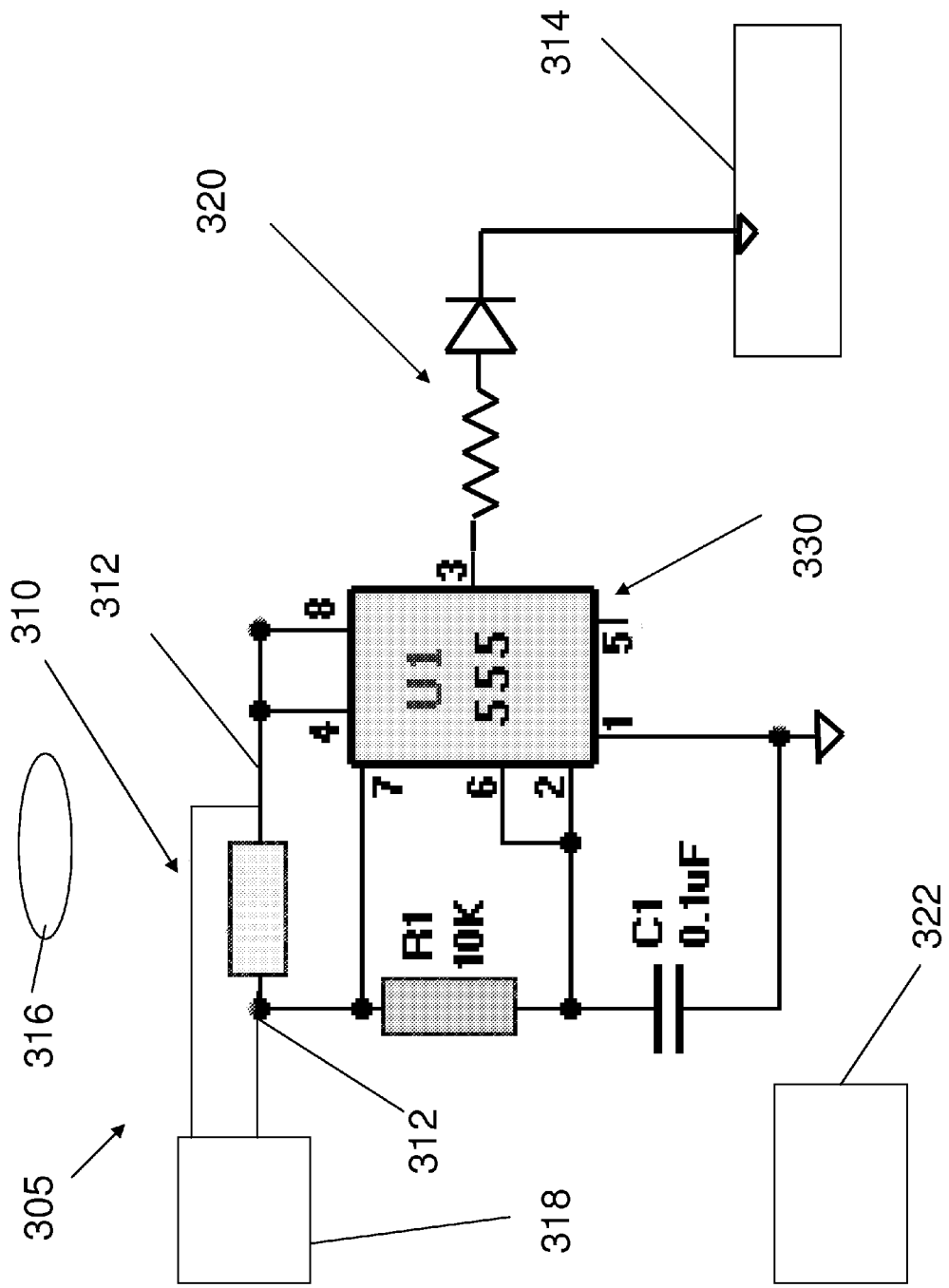
FIG. 6 is a conceptual illustration of a chemical switch in combination with the chemical resistor sensor shown in FIG. 5.

Referring to FIG. 6, in one exemplary embodiment, the sensor 310 may be packaged into an appropriate detector circuit which would activate only following transduction of the sensor 310 from a high-resistance state to a to low-resistance state. While not wishing to be bound by theory, it is believed that the battery life of the sensor device 310 would thereby be virtually infinite and the sensor 310 stands ready without the need for routine maintenance. Moreover, while not wishing to be bound by theory, it is believed that the sensor device 310 uses <1 uW of power. Thus, the sensor 310 can serve as a passive monitoring system 314; while at the same time provide an electronic signal that may be used in certain embodiments as a chemical switch 305. Such an electronic response has numerous advantages in that it can be i) used to trigger an audio or visual alarm, ii) interfaced to a telemetry system 322 for remote monitoring; iii) electronically stored and/or directly recorded in real-time for record keeping or analyses. Furthermore, there is less manual operation associated with an automated electronic monitor relative to passive colorimetric indicators and at extremely low cost and small size. In one embodiment, the chemical sensor 305 may comprise a reading means 316 and a measuring means 318 for both the electronic and visual changes in the film layer 410.

Other applications for the chemical resistor sensor include, but are not limited to, fertilizer manufacture and boiler feed water anti-oxidant and in military [ballistic missiles propellant; and satellite propellant]. The chemical resistor sensor may also be employed as a passive leak detector over pneumatic fittings. The chemical resistor sensor may also be mounted on a clip that "snaps" over pneumatic lines and fittings.

Figure 4:
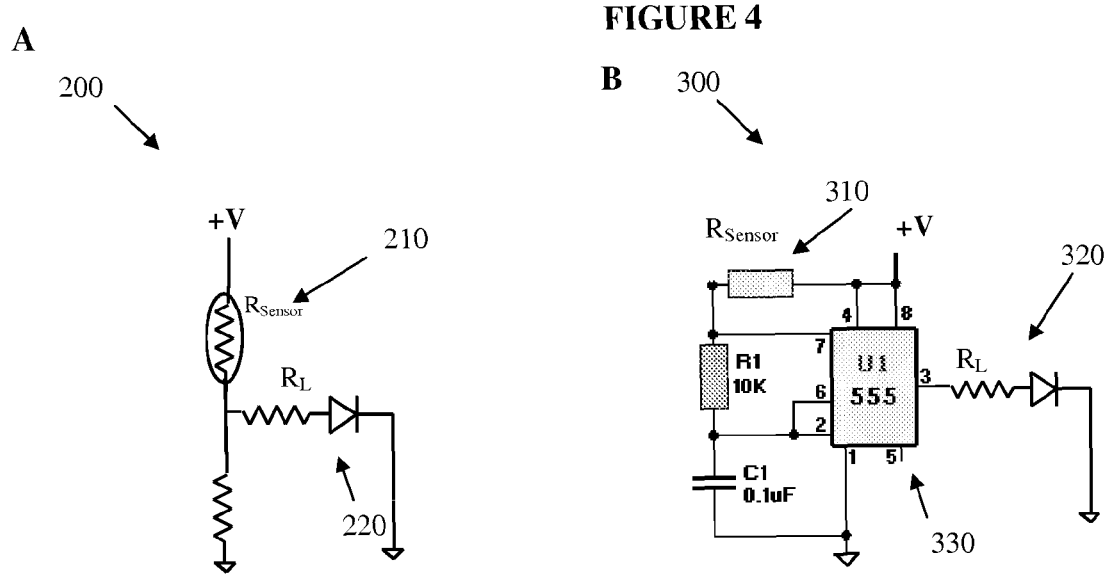
FIG. 4 illustrates simple electronic circuits used for the chemical resistor sensor readout according to one embodiment of the present invention.

FIGS. 3 and 4 illustrates exemplary electronic circuits utilized for the chemical resistor readout according to one embodiment of the present invention.

One exemplary circuit 200 is illustrated in FIG. 4A. In this embodiment, $R_S$ is the chemical sensor 210 and $R_L$ is the load for an alarm circuit 220. For example, the alarm circuit may comprise an LED. As an insulation $R_S$ 210 prevents current flow and the potential across $R_L$ 220 is zero (no alarm). Upon exposure, $R_S$ 210 drops in value and thereby inducing a voltage drop across $R_L$ 220 (alarm).

Another exemplary circuit 300 is illustrated in FIG. 3B. In this embodiment, a timer chip 330, such as a 555 timer chip is utilized before the load for the alarm circuit 320. In this embodiment, faster rates from the timer chip 330 would correspond to higher concentrations of hydrazine.

In another embodiment, prior to exposure, the circuit has near-zero electric power requirement. The output signal could interface to an audible alarm circuit or to a telemetry system for remote monitoring or may be adapted as an area monitor.

In summary, the chemical resistor sensor described above is a passive device and requires no external power supply for transduction. The device requires no moving parts, and prior to vapor exposure draws negligible electrical power (less than a fraction of a microampere), therefore can be deployed for extended time under battery operation. The actual transduction process (for example, the electrochemical reduction of the gold salt) occurs passively as well. Thus, the device can be configured to operate in potentially explosive environments. This device provides a low-cost, efficient passive monitor for fugitive analyte emissions.

Properties of the Hydrazine Chemical Resistor Sensor:

| | | |
|---|---|---|
| No Vapor Exposures: | >1,000 KΩ (1 MΩ) | Yellow Color |
| Post vapor exposures: | <500 Ω (typically <50 Ω) | Black Color |
| Interferants | none known | |
| Shelf life | >1 yr - prototype structures were stable for greater than 1 year | Range of "Observation" |
| Calorimetric Indicator: | 5 feet (eyesight range) | |
| Chemi-resistor with LED alarm: | 25 feet (illuminated signal) | |
| Chemi-resistor with Telemetry | at home or any remote site | |
| Power Requirements: | Negligible prior to exposure | |

EXAMPLES

Example 1

Figure 2:
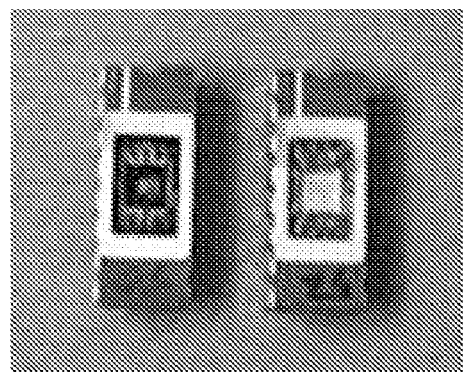
FIG. 2 is a photograph of a chemical resistor sensor according to one embodiment of the present invention.

FIG. 2 illustrates a chemical resistor sensor configured to measure the changes in electrical properties upon exposure to hydrazine vapor. The device is mounted in a low-cost commercially available header configured in a standard 16-pin DIP package. The chemical resistor sensor comprises an electrochemical reduction of a gold salt loaded onto a low-cost commercial substrate containing two or more noble metal electrodes.

Left Side: Upon interaction with hydrazine vapor, a dark color forms and the device is very conductive. Right Side: Unexposed, the device is a light yellow color and is very resistive; In one embodiment, chemically sensitive film comprises a polymer that stabilizes the chemically sensitive layer so it can last a long time, an important feature not found in prior art devices that seem to be relatively short lived;

For the device described herein, the gold salt chemical reagent is suspended in a thin polymer medium and then is applied to a substrate layer comprising two or more electrodes. To prepare the polymer medium, polystyrene or other polymer systems is first dissolved in DMF solvent. Gold salt is then added to the solution such that the weight of the salt is between about 2 to about 10% of the polymer medium. Since the gold salt is not soluble in the DMF solvent, the mixture is sonicated to form a homogenous suspension of the insoluble salt in the DMF/polymer medium solution. Aliquots of the suspension are then applied to the electrodes. Upon evaporation of the solvent, a thin solid but permeable polymer film with embedded gold salt is formed on the substrate layer. The polymer provided not only a physical matrix to contain the salt that still allowed analyte vapors access, but also provided significant shelf-life stability by protecting against photo and moisture induced degradations. A shelf-life of over one year is obtained without any special storage requirements.

Once properly configured, the change in electrical property induced specifically by hydrazine can be quite dramatic. The initial resistance of the chemical resistor sensor is greater than 1 M-ohm (beyond the limits of the measurement meter used in this example). Following exposure to hydrazine vapors there is the expected color change in the chemical reagent. However, more importantly, upon exposure to hydrazine the resistance drops to less than 500 ohms; the magnitude of the change may vary from device to device and extent of exposure. As shown in FIG. 3, voltametric measurements from +200 to −200 mV indicate that this change is purely resistive.

One unique aspect of this sensor is that since it is an electronic insulator prior to hydrazine vapor exposure, it can be configured such that it draws electric power only after hydrazine vapor exposure. Both the optical and electrical transformation is spontaneous and both are observed simultaneously and both are dependent upon amount of hydrazine vapor exposure. No other chemical is found to induce a comparable change, although, while not wishing to be bound by theory, it is expected that only those compounds that can reduce the salt would respond to the chemical resistor sensor of this example.

The chemical resistor sensor can serve as a passive monitor, lasting almost indefinitely under battery power while at the same time provide an immediate electronic signal that can be used to monitor for leaks and exposure. Therefore, the sensor device illustrated in FIG. 2 can operate both as a passive visual detector and a passive electronic device.

Example 2

In an informal experiment, two identical chemical resistor sensors are simultaneously stored in a 250 mL sealed glass bottle. One sensor is exposed to high ppm levels of hydrazine vapors, while the second device is not exposed to hydrazine vapors. During the overnight storage period, outgassing vapors from the exposed device induce a response in the unexposed device. Although quantitative assessment is not possible in this observation, it is likely that the vapor level with the bottle was quite low, probably significantly less than 1 ppm. It is probable that there is a time delay or dosimeter effect (i.e. high concentration will react quickly and low concentration will react over longer time). Similarly, it is believed that devices with high salt concentration will sense low levels and devices with low salt levels will be good for high concentrations and the optimum mixtures need to be determined for this technology.

Example 3

A chemical resistor sensor is readily interfaced to a detection circuit design to respond to changes in resistance. A simple logging digital voltmeter serves as a detection circuit for evaluation in the engineering lab or in the field. Since the chemical resistor sensor is an insulator, it may be easy to configure an electronic circuit that can interface to conventional external DAQ systems and/or to interface to some form of external alarm with the chemical resistor sensor. Indeed since negligible current flows through the sensor in the insulating state, such a circuit can run for extended periods under battery power. FIG. 4 illustrates simple, low cost and low power voltage divider circuit designs.

The foregoing description of embodiments and examples of the invention has been presented for purposes of illustration and description. It is not intended to be exhaustive or to limit the invention to the forms described. Numerous modifications are possible in light of the above teachings. Some of those modifications have been discussed and others will be understood by those skilled in the art. The embodiments were chosen and described in order to best illustrate the principles of the invention and various embodiments as are suited to the particular use contemplated. The scope of the invention is, of course, not limited to the examples or embodiments set forth herein, but can be employed in any number of applications and equivalent devices by those of ordinary skill in the art. Rather it is hereby intended the scope of the invention be defined by the claims appended hereto.

What is claimed is:

1. A chemical sensor comprising: (1) a film layer comprising at least one chemical reagent dispersed in a medium and (2) a substrate layer comprising at least two electrodes, wherein the chemical reagent is an insulator noble metal salt before interaction with an analyte and transforms into a conductive metallic material after interaction with the analyte and produces a visual change and an electronic change, wherein the visual change comprises an optical change in the film layer, and wherein the electronic change comprises a change in the electrical resistance, capacitance, or impedance of the film layer.

2. The chemical sensor of claim 1, comprising a means for reading and/or measuring both the electronic and visual changes in the film layer.

3. The chemical sensor of claim 1, wherein the medium is a dielectric and/or stabilizing medium.

4. The chemical sensor of claim 1, wherein the medium comprises a polymer.

5. The chemical sensor of claim 1, wherein the electronic change is at least partially reversible.

6. The chemical sensor of claim 1, wherein the chemical sensor utilizes less than about 1 μW of power.

7. A chemical sensor comprising: (1) a film layer comprising at least one noble metal salt dispersed in a polymer medium and (2) a substrate layer comprising at least two electrodes, wherein the insulator noble metal salt upon interaction with an analyte transforms into a conductive metallic material and produces a visual change and an electronic change, wherein the visual change comprises an optical change in the film layer, and wherein the electronic change comprises a change in the electrical resistance, capacitance, or impedance of the film layer.

8. The chemical sensor of claim 7, comprising a means for reading and/or measuring the electronic and visual changes in the film layer.

9. A chemical sensor comprising: (1) a film layer comprising $KAuCl_4$ dispersed in a polymer medium and (2) a substrate layer comprising at least two electrodes, wherein $KAuCl_4$ transforms into a conductive metallic material after interaction with a strong reducing agent to produce a visual change and an electronic change, wherein the visual change comprises an optical change in the film layer, and wherein the electronic change comprises a change in the electrical resistance, capacitance, or impedance of the film layer.

10. The sensor of claim 9, wherein the reducing agent is selected from the group consisting of hydrazine, monomethylhydrazine, unsymmetric hydrazine and combinations thereof.

11. The chemical sensor of claim 9, wherein the film layer is formed by the process comprising: (1) mixing a polymer in a solvent to form a distributed polymer medium; (2) adding $KAuCl_4$ to the distributed polymer medium to form a mixture; (3) applying the mixture to the substrate layer; and (4) evaporating the solvent in the mixture to form the film layer.

12. The chemical sensor of claim 11, wherein the mixture comprises homogenously dispersed $KAuCl_4$ within the polymer medium.

13. The chemical sensor of claim 9, wherein $KAuCl_4$ comprises from about 2 to about 10 weight percent of the polymer medium.

14. The chemical sensor of claim 9, wherein the film layer is permeable to the strong reducing agent.

15. The chemical sensor of claim 9, wherein the polymer comprises polystyrene, polyethylene, polypropylene, polyvinyl alcohol, polyvinylidine and/or a combination thereof.

16. The chemical sensor of claim 9, wherein the ratio of $KAuCl_4$ to the polymer is from about 1 to about 1.

17. The chemical sensor of claim 9, wherein the visual change is irreversible.

18. The chemical sensor of claim 9, wherein the electronic change comprises a change in the electrical resistance, wherein the electrical resistance prior to the reaction is greater than about 10 MΩ and wherein the electrical resistance after the reaction is from about 50 to less than about 5000Ω.

19. The chemical sensor of claim 9, wherein the substrate layer comprises micro-fabricated substrates.

20. The chemical sensor of claim 9, wherein the electronic change comprises a change in the electrical resistance, wherein the electrical resistance prior to the reaction is greater than about 1 MΩ and the electrical resistance after the reaction is less than about 50Ω.

21. The chemical sensor of claim 7, wherein the reaction occurs within seconds upon interaction and the reaction is complete in about 5 minutes.

22. A chemical switch comprising the chemical sensor of claim 7.

23. The chemical switch of claim 22, wherein upon reaction a visual and/or audible alarm, a second monitoring system, a telemetry system or any combination thereof is activated.

* * * * *